(12) United States Patent
Voss et al.

(10) Patent No.: US 6,706,162 B1
(45) Date of Patent: Mar. 16, 2004

(54) HIGH SPEED, HIGH RESOLUTION COMPOSITIONS, METHODS, AND KITS FOR CAPILLARY ELECTROPHORESIS

(75) Inventors: Karl O. Voss, San Mateo, CA (US); Aldrich N. K. Lau, Palo Alto, CA (US)

(73) Assignee: Applera Corporation, Foster City, CA (US)

( * ) Notice: Subject to any disclaimer, the term of this patent is extended or adjusted under 35 U.S.C. 154(b) by 55 days.

(21) Appl. No.: 09/668,960

(22) Filed: Sep. 25, 2000

(51) Int. Cl.$^7$ .......................... B01D 57/02; B01D 59/42; B01D 59/50; B01D 61/42; B01D 61/58; C02F 1/469; C07K 1/26; C08F 2/58

(52) U.S. Cl. ........................................ 204/455
(58) Field of Search ........................ 204/455

(56) References Cited

U.S. PATENT DOCUMENTS

| | | | |
|---|---|---|---|
| 5,089,111 A | | 2/1992 | Zhu et al. |
| 5,264,101 A | * | 11/1993 | Demorest et al. ........... 204/452 |
| 5,374,527 A | | 12/1994 | Grossman |
| 5,552,028 A | | 9/1996 | Madabhushi et al. |
| 5,741,411 A | | 4/1998 | Yeung et al. |
| 5,779,868 A | | 7/1998 | Parce et al. |
| 6,322,682 B1 | * | 11/2001 | Arvidsson et al. .......... 204/451 |

FOREIGN PATENT DOCUMENTS

| | | |
|---|---|---|
| WO | WO 00/28314 | 5/2000 |
| WO | WO 00/42423 A1 | 7/2000 |

OTHER PUBLICATIONS

Carrilho et al., 1996, "Rapid DNA Sequencing of More Than 1000 Bases per Run by Capillary Electrophoresis Using Replaceable Linear Polyacrylamide Solutions," *Analytical Chemistry*, 68:3305–3313.

Chiari et al., 1998, "Separation of oligonucleotides and DNA fragments by capillary electrophoresis in dynamically and permanently coated capillaries, using a copolymer of acrylamide and β–D–glucopyranoside as a new low viscosity matrix with sieving capacity," *Electrophoresis*, 19:3154–3159.

Chiari et al., 2000, "New adsorbed coatings for capillary electrophoresis," *Electrophoresis*, 21:909–916.

Chiari et al., "Separation of Oligonucleotides and DNA Fragments in Coated and Uncoated Capillaries Filled with New Replaceable Low–Viscosity Matrices," Abstracts: Monday Lecture, Institute of Chimica degli Ormoni, CNR, Milano, Italy.

Glass, Editor, 1986, *Water–Soluble Polymers—Beauty with Performance*, Advances in Chemistry Series, Developed from a symposium sponsored by the Division of Polymeric Materials Science and Engineering at the 188$^{th}$ Meeting of the American Chemical Society, Philadelphia, Pennsylvania, Aug. 26–31, 1984 (Table of Contents and Index).

Molyneux, 1984, *Water–Soluble Synthetic Polymers: Properties and Behavior*, vol. I & II, CRC Press, Inc., Boca Raton, Florida, (Table of Contents and Index).

Salas–Solano et al., 1998, "Routine DNA Sequencing of 1000 Bases in Less Than One Hour by Capillary Electrophoresis with Replaceable Linear Polyacrylamide Solutions," *Analytical Chemistry*, 70:3996–4003.

(List continued on next page.)

*Primary Examiner*—Mark L. Bell
*Assistant Examiner*—Jennine Brown

(57) ABSTRACT

The invention provides compositions, methods and kits for high speed, high resolution of analytes by capillary electrophoresis starting with uncoated capillaries. The compositions comprise a sieving component, comprising a non-crosslinked acrylamide polymer, and a surface interaction component, comprising at least one uncharged and non-crosslinked water-soluble silica-adsorbing polymer. Methods for employing the novel compositions in capillary electrophoresis are provided. Kits comprising the novel compositions for use in the novel methods are also provided.

21 Claims, 4 Drawing Sheets

OTHER PUBLICATIONS

Takagi, 1990, "Application of low–angle laser light scattering detection in the field of biochemistry," *Journal of Chromatography*, 506:409–416.

Wyatt, 1993, "Light scattering and the absolute characterization of macromolecules," *Analytica Chimica Acta*, 272:1–40.

Wyatt, 1997, "Multiangle light scattering: The basic tool for macromolecular characterization," *Instrumentation Science & Technology*, 25(1):1–18.

Zhou et al., 2000, "DNA Sequencing up to 1300 Bases in Two Hours by Capillary Electrophoresis with Mixed Replaceable Linear Polyacrylamide Solutions," *Analytical Chemistry*, 72:1045–1052.

Liang, Dehai et al., "High speed separation of DNA fragments by capillary electrophoresis in poly(ethylene oxide)–poly (propylene oxide)–poly(ethylene oxide) triblock polymer." *Electrophoresis*, 19:2447–2453 (1998).

International Search Report for PCT Application No. PCT/US01/42271, mailed Sep. 25, 2002.

Chiari et al., "Separation of Oligonucleotides and DNA Fragments in Coated and Uncoated Capillaries Filled with New Replaceable Low–Viscosity Matrices," Abstracts: Monday Lecture, Institute of Chimica degli Ormoni, CNR, Milano, Italy. No date available.

Heller, Christoph et al., "Finding a universal low viscosity polymer for DNA separation (II)," *Electrophoresis*, 19:3114–3127 (1998).

PCT Written Opinion for PCT Application No. PCT/US01/42271, mailed May 21, 2003.

* cited by examiner

HIGH SPEED, HIGH RESOLUTION COMPOSITIONS, METHODS, AND KITS FOR CAPILLARY ELECTROPHORESIS

FIELD OF THE INVENTION

The inventions relate to compositions, capillary electrophoresis elements, and methods for separating analytes by capillary electrophoresis. Kits for separating analytes by capillary electrophoresis are also provided.

BACKGROUND OF THE INVENTION

Capillary electrophoresis has been applied widely as an analytical technique because of several technical advantages: (i) capillaries have high surface-to-volume ratios which permit more efficient heat dissipation which, in turn, permit high electric fields to be used for more rapid separations; (ii) the technique requires minimal sample volumes; (iii) superior resolution of most analytes is attainable; and (iv) the technique is amenable to automation, see, e.g., Camilleri, editor, Capillary Electrophoresis: Theory and Practice (CRC Press, Boca Raton, 1993); and Grossman et al., editors, Capillary Electrophoresis (Academic Press, San Diego, 1992). Because of these advantages, there has been great interest in applying capillary electrophoresis to the separation of biomolecules, particularly nucleic acids. The need for rapid and accurate separation of nucleic acids, particularly deoxyribonucleic acid (DNA) arises in the analysis of polymerase chain reaction (PCR) products and DNA sequencing, see, e.g., Williams, Methods: A Companion to Methods in Enzymology, 4: 227–232 (1992); Drossman et al., Anal. Chem., 62: 900–903 (1990); Huang et al., Anal. Chem., 64: 2149–2154 (1992); and Swerdlow et al., Nucleic Acids Research, 18: 1415–1419 (1990).

Since the charge-to-frictional drag ratio is the same for different sized polynucleotides in free solution, electrophoretic separation of polynucleotides typically involves a sieving medium. The initial sieving media of choice were typically crosslinked gels, but in some instances problems of stability and manufacturability have led to the examination of non-gel liquid polymeric sieving media, such as linear polyacrylamide, hydroxyalkylcellulose, agarose, and cellulose acetate, and the like, e.g., Bode, Anal. Biochem., 83: 204–210 (1977); Bode, Anal. Biochem., 83: 364–371 (1977); Bode, Anal. Biochem., 92: 99–110 (1979); Hjerten et al., J. Liquid Chromatography, 12: 2471–2477 (1989); Grossman, U.S. Pat. No. 5,126,021; Zhu et al., U.S. Pat. No. 5,089,111; Tietz et al., Electrophoresis, 13: 614–616 (1992).

Another factor that may complicate separations by capillary electrophoresis is the phenomena of electroendoosmosis. This phenomena, sometimes referred to as electroosmosis or electroendoosmotic flow (EOF), is fluid flow in a capillary induced by an electrical field. This phenomenon has impeded the application of capillary electrophoresis to situations where high resolution separations typically are sought, such as in the analysis of DNA sequencing fragments. The phenomena can arise in capillary electrophoresis when the inner wall of the capillary contains immobilized charges. Such charges can cause the formation of a mobile layer of counter ions which, in turn, moves in the presence of an electrical field to create a bulk flow of liquid. Unfortunately, the magnitude of the EOF can vary depending on a host of factors, including variation in the distribution of charges, selective adsorption of components of the analyte and/or separation medium, pH of the separation medium, and the like. Because this variability can reduce one's ability to resolve closely spaced analyte bands, many attempts have been made to directly or indirectly control such flow. The attempts have included covalent coating or modification of the inner wall of the capillary to suppress charged groups, use of high viscosity polymers, adjustment of buffer pH and/or concentration, use of a gel separation medium for covalently coating the capillary wall, and the application of an electric field radial to the axis of the capillary.

Currently, capillary electrophoresis of nucleic acid fragments is often performed using precoated capillaries. Precoated capillary tubes typically are expensive to make, have a limited lifetime, and can be subject to reproducibility problems. These problems are particularly important with large scale capillary electrophoresis using multiple capillaries run in parallel.

SUMMARY OF THE INVENTION

The present invention provides compositions for separating analytes in a sample. For example, single-base resolution of DNA sequencing fragments or other polynucleotide fragments. Compositions are provided that comprise a sieving component, comprising at least one low viscosity, high molecular weight non-crosslinked acrylamide polymer, and optionally, a surface interaction component, comprising at least one non-crosslinked polymer. In a preferred embodiment, the compositions do not comprise a crosslinked polymer gel.

In another aspect, the present invention comprises a capillary electrophoresis element. The capillary electrophoresis element comprises an uncoated capillary into which is inserted a composition for separating analytes. The composition located within the capillary comprises a sieving component and a surface interaction component.

In another aspect, methods are provided wherein the compositions of the invention are employed for separating analytes by capillary electrophoresis. In certain embodiments, the methods of the invention are carried out in parallel using a plurality of uncoated capillaries or capillary electrophoresis elements containing the novel compositions disclosed herein.

In another aspect, the invention provides compositions comprising a low viscosity, high molecular weight non-crosslinked acrylamide polymer sieving component without a surface interaction component for use with, among other things, precoated capillaries. Precoated capillaries are commercially available, for example, from Bio-Rad Life Sciences (e.g., Biocap XL capillaries, catalog no. 148–3081). Capillaries may also be precoated using methods well known in the art. Such procedures are described in, for example, Cobb et al., Anal. Chem. 62:2478 (1990), and Grossman, U.S. Pat. No. 5,347,527.

Kits for separating analytes by capillary electrophoresis are also provided. In certain embodiments, the kits comprise one of the compositions provided herein. Kits comprising uncoated capillaries for use with one or more of these compositions or methods are also provided.

BRIEF DESCRIPTION OF THE DRAWINGS

FIG. 1A (top) shows a graph of the single base resolution versus fragment size, measured in nucleotide bases. FIG. 1B shows a graph of the fragment migration time, in minutes, versus the fragment size, measured in nucleotide bases.

FIG. 2A (top) shows a graph of single base resolution versus fragment size, measured in nucleotide bases. FIG. 2B shows a graph of the fragment migration time, in minutes, versus the fragment size, measured in nucleotide bases.

FIG. 3A (top) shows a graph of the single base resolution versus fragment size, measured in nucleotide bases. FIG. 3B shows a graph of the fragment migration time, in minutes, versus the fragment size, measured in nucleotide bases.

DEFINITIONS

Figure 1:
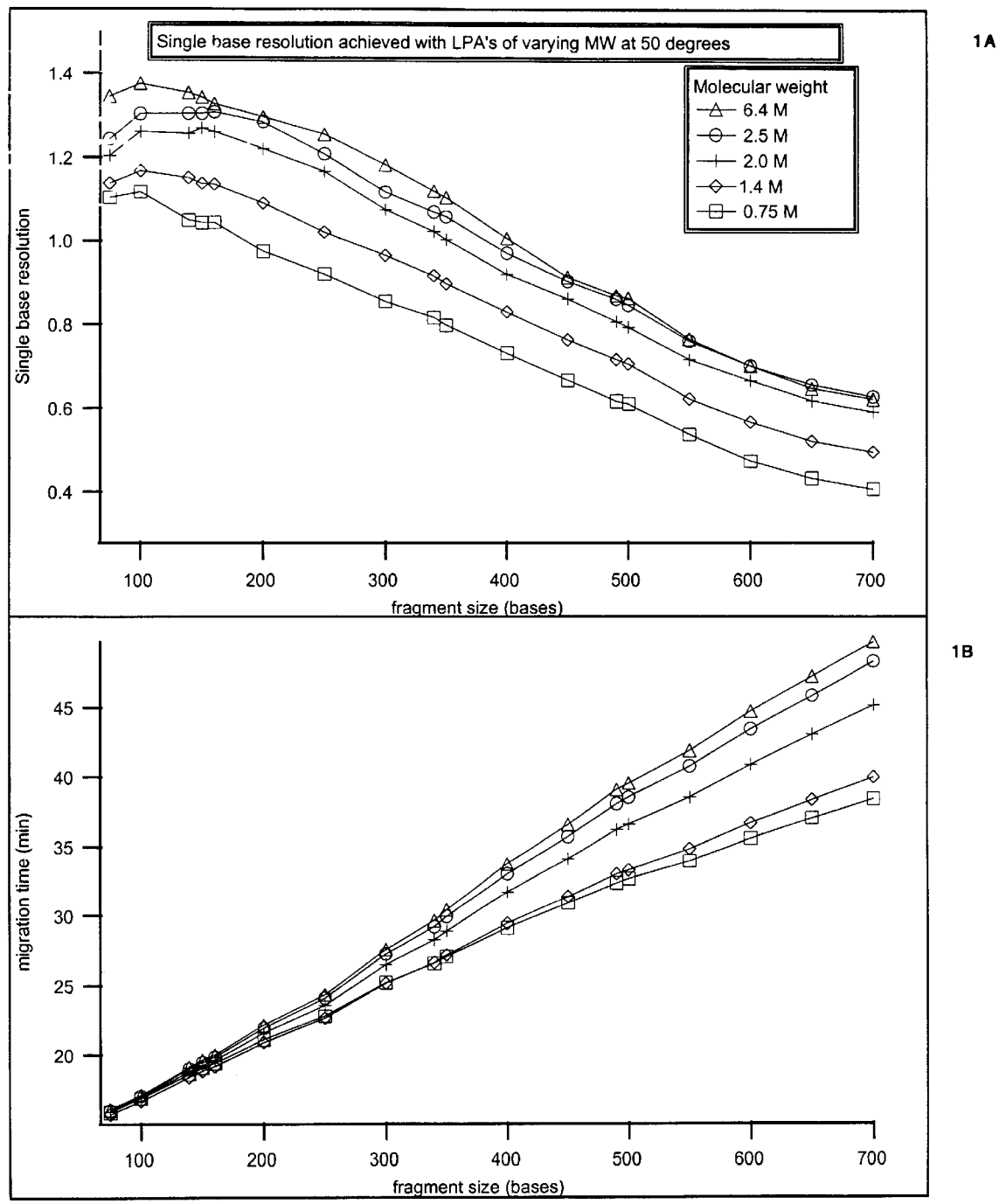
FIG. 1 illustrates single base resolution data collected by capillary electrophoresis of labeled polynucleotide molecular weight ladders using run temperature of 50° C. and compositions comprising non-crosslinked acrylamide polymer sieving components with average molecular weights of approximately 744,000 daltons (Da) (0.75 M); 1,376,000 Da (1.4 M); 2,015,000 Da (2.0 M); 2,517,000 Da (2.5 M); or 6,377,000 Da (6.4 M).

"Acrylamide" and "acrylamide monomer" refers to a structure having the formula $H_2C=CR—C(=O)NR_1R_2$, where R can be —H or —$CH_3$, $R_1$ and $R_2$ can be independently —H, —$CH_3$, —$(CH_2)_xOH$, —$CH_2CH(OH)$ $(CH_2)_yOR_3$, —$CH(CH_2OH)CH(OH)CH_3$, —$CH_2CH_2$ $(OCH_2CH_2)_p$—$OR_3$, —$CH_2CONH_2$,

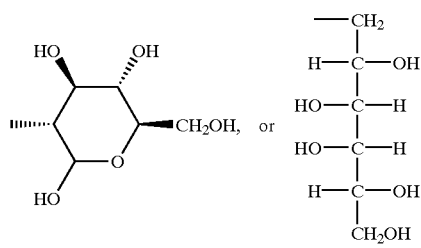

and $R_3$ can be independently —H, —$CH_3$, or —$CH_2CH_3$. The values for x and y range from 1 to 3 and the value of p ranges from 1 to 200.

"Average molecular weight" refers to the weight-average molecular weight ($M_w$) of a sample population made up of polymer species having a multiplicity of molecular weights. This quantity is defined by the equation:

$$M_w = \left(\sum_{i=1}^{n} n_i \times (M_i)^2\right) \Big/ \sum_{i=1}^{n} n_i \times M_i$$

where $n_i$ indicates the number of molecules of species i and $M_i$ is the molecular weight of $i^{th}$ species. As used herein, the term "molecular weight" refers to weight average molecular weight, unless otherwise specified.

The term "capillary" as used herein, refers to a tube or channel or other structure for carrying out electrophoresis that is capable of supporting a volume of separation medium, such as a composition for separating analytes, as disclosed herein. The geometry of a capillary may vary widely and includes, but is not limited to, tubes with circular, rectangular or square cross-sections, channels, grooves, plates, and the like, and may be fabricated by a wide range of technologies. An important feature of a capillary for use with certain embodiments of the invention is the surface-to-volume ratio of the surface in contact with the volume of separation medium. High values of this ratio typically permit better heat transfer from the separation medium during electrophoresis. Preferably, in certain embodiments, values in the range of about 0.8 to 0.02 $m^{-1}$ are employed. These correspond to the surface-to-volume ratios of tubular capillaries with circular cross-sections having inside diameters in the range of about 5 μm to about 200 μm. The term "uncoated capillary" means that the capillary is uncoated prior to the introduction of compositions of the invention, i.e., not covalently coated prior to use. In certain embodiments, capillaries for use with the invention are made of silica, fused silica, quartz, silicate-based glass, such as borosilicate glass, phosphate glass, alumina-containing glass, and the like, or other silica-like materials. In certain embodiments, capillaries formed in plastic substrates are used. Plastic substrates may comprise, for example, poly-acrylates and polyolefins, such as LUCRYL® (BASF, Germany), TPX™ (Matsui Plastics, Inc., White Plains, N.Y.), TOPAS™ (Hoechst Celanese Corp., Summit, N.J.), and ZEONOR® (Zeon Chemicals, Louisville, Ky.). Descriptions of plastic substrates for channel capillaries may be found, among other places, in U.S. Pat. No. 5,750,015.

As used herein, the term "composition for separating analytes" comprises a low viscosity, high molecular weight sieving component and optionally, a surface interaction component. Such compositions are particularly useful for separating polynucleotides, or other biomolecules having different sizes but similar or identical charge-frictional drag ratios in free solution using capillary electrophoresis. The skilled artisan will appreciate that a charge-carrying component, or electrolyte is typically included in such compositions. The charge-carrying component is usually part of a buffer system for maintaining the separation medium at a constant pH. The compositions for separating analytes contain one or more non-crosslinked acrylamide polymers.

The term "DNA sequencing fragments" refers to DNA polynucleotides generated for the purpose of obtaining sequence information about a selected DNA target sequence. Such fragments can be generated enzymatically, e.g., by the Sanger dideoxy method, or chemically, e.g., by the Maxam and Gilbert method. The fragments may originate in a single sequencing reaction (e.g., a dideoxy sequencing reaction performed in the presence of dideoxycytidine tripohophate), or from more than one sequencing reaction (e.g., from four different dideoxy sequencing reactions which include suitably labeled 5'-primers to identify the 3'-terminal base of each fragment).

"Polymer" is used in its traditional sense, referring to a large molecule composed of smaller monomeric or oligomeric subunits covalently linked together to form a chain. A "homopolymer" is a polymer made up of only one monomeric repeat unit. A "copolymer" refers to a polymer made up of two or more kinds of monomeric repeat unit. Linear polymers are composed of monomeric repeat units linked together in one continuous length to form polymer molecules. Branched polymers are similar to linear polymers but have side chains protruding from various branch points along the main polymer. Star-shaped polymers are similar to branched polymers except that multiple side branches radiate from a single branch site, resulting in a star-shaped or wheel-and-spoke appearance.

Crosslinked polymers contain, for example, polymer molecules that are i covalently linked to each other at points other than at their ends. Crosslinking can occur during the polymerization process in the presence of crosslinking agents. At some degree of crosslinking, known as the gel point, gelation occurs. At the gel point, a visible gel or insoluble polymer forms and the system tends to lose fluidity. This crosslinked polymer gel, which corresponds to the formation of a network of polymer molecules that are crosslinked to form a macroscopic molecule, is insoluble in all solvents, even at elevated temperatures. Discussion of acrylamide polymers and polymer gels may be found in references known in the art, for example, Odian, Principles of Polymerization, Third Edition (Wiley Interscience, 1991).

As used herein, the term "non-crosslinked acrylamide polymer" refers to polymer molecules comprising acrylamide monomers, with or without branching, but excluding polymer molecules that are crosslinked together. Thus, a non-crosslinked polymer does not contain polymer molecules that are linked at points other than their end, and does not undergo gelation during polymerization.

The term "polynucleotide" as used herein refers to linear polymers of natural or modified nucleoside monomers, including double and single stranded deoxyribonucleosides, ribonucleosides, -anomeric forms thereof, and the like. Typically, the nucleoside monomers are linked by phosphodiester bonds or analogs thereof to form polynucleotides, however, peptide nucleic acids are also contemplated. In certain embodiments, polynucleotides range in size from a few monomeric units, e.g., 20, to several thousands of monomeric units. Whenever a polynucleotide is represented by a sequence of letters, such as "ATGCCTG," it will be understood that the nucleotides are in 5'=>3' order from left to right and that "A" denotes deoxyadenosine, "C" denotes deoxycytidine, "G" denotes deoxyguanosine, and "T" denotes deoxythymidine, unless otherwise noted. Analogs of phosphodiester linkages include phosphothioate, phosphodithioate, phosphoselenate, phosphodiselenate, phosphoroanilothioate, phosphoranilidate, phosphooramidite, and the like.

The term "single base resolution" ($R_{singlebase}$) refers to the measurement of resolution between two peaks arising from two polynucleotide fragments that differ in size by one nucleotide. Single base resolution can be determined mathematically using the formula:

$$R_{singlebase} = 2 \times \frac{t_n - t_{n+1}}{W_n + W_{n+1}}$$

where $t_n$ is the migration time of a polynucleotide fragment that is n nucleotides in length; $t_{n+1}$ is the migration time of a polynucleotide fragment n+1 nucleotides in length; $W_n$ is the full width at the base of the peak from the polynucleotidel fragment n nucleotides in length; and $W_{n+1}$ is the full width at the base of the peak from the polynucleotide fragment n+1 nucleotides in length. "Migration time" is the time that it takes for a polynucleotide fragment to travel the length of the capillary or microchannel, i.e., from the injection point to the detector.

The term "single base resolution limit" refers to the size of a polynucleotide fragment where the single base resolution value drops below 0.58 in a particular system.

DETAILED DESCRIPTION OF EXEMPLARY EMBODIMENTS

The section headings used herein are for organizational purposes only and are not to be construed as limiting the subject matter described. All references cited in this application are expressly incorporated by reference for any purpose to the same extent as if each reference was specifically and individually incorporated by reference.

In certain embodiments, the invention provides compositions comprising a low viscosity, high molecular weight non-crosslinked acrylamide polymer sieving component. In other embodiments, compositions further comprise a surface interaction component, such as polydimethylacrylamide (pDMA). Furthermore, the compositions of the invention does not include a crosslinked polymer gel. Methods are provided for high speed, high resolution capillary electrophoresis of analytes, particularly polynucleotide sequences, by using the novel compositions. Kits for employing these methods are also provided.

One benefit of the compositions of the invention is that non-crosslinked acrylamide polymers with a molecular weight of between 1,000,000 Da and 3,000,000 Da provide unexpected advantages when used in the disclosed methods and electrophoresis elements compared to known electrophoretic compositions. Linear acrylamide polymers with molecular weights less than about 1,000,000 Da provide poorer resolution than the compositions of the invention. Linear acrylamide polymers with molecular weights greater than about 3,000,000 Da present viscosity problems and are hard to manipulate, e.g., to insert into and remove from capillaries. Thus, the compositions of the invention have a viscosity at 25° C. of less than 10,000 centipoise, preferably less than 5,000 centipoise, more preferably less than 1,000 centipoise, and most preferably less than 600 centipoise. Non-crosslinked acrylamide polymers may include, for example, linear polymers such as polyacrylamide (LPA), branched polymers, and star-shaped polymers.

The sieving component may comprise hydrophilic N-substituted acrylamide polymers (i.e., the substituent is attached to the acrylamide nitrogen) other than polyacrylamide. Exemplary hydrophilic N-substituted acrylamide polymers include the following homopolymers and their copolymers:

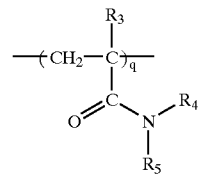

where $R_3$ can be —H or —$CH_3$, $P_4$ and $R_5$ can be independently —H, —$CH_3$, —$(CH_2)_xOH$, —$CH_2CH(OH)$ $(CH_2)_yOR_6$, —$CH(CH_2OH)CH(OH)CH_3$, —$CH_2CH_2$ $(OCH_2CH_2)_pOR_6$, —$CH_2CONH_2$,

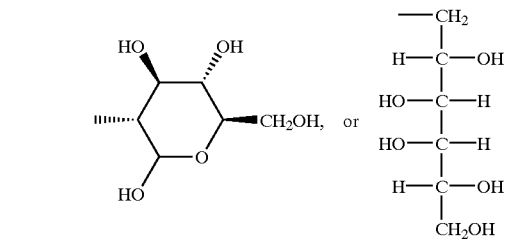

and $R_6$ can be independently —H, —$CH_3$, or —$CH_2CH_3$. The values for x and y range from 1 to 3, the value of p ranges from 1 to 200, and q is directly proportional to the molecular weight of the polymer and ranges from a few hundred to hundreds of thousands. The average molecular weight ranges from 100,000 Da to 25,000,000 Da, preferably from 1,000,000 Da to 3,000,000 Da.

One exemplary hydrophilic N-substituted acrylamide copolymer suitable for use as a sieving component in the disclosed compositions is:

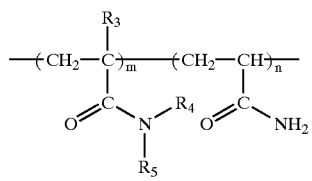

where, $R_3$, $R_4$, $R_5$, and the molecular weight of copolymers, are as previously described, and the ratio of m:n ranges from about 100:1 to about 1:100.

In certain embodiments, the sieving component comprises a non-crosslinked acrylamide polymer having an average molecular weight between about 1,000,000 Da and 3,000,000 Da. Non-crosslinked acrylamide polymers with average molecular weights of 1,000,000 Da or greater provide improved resolution. Non-crosslinked acrylamide polymers with average molecular weights of 3,000,000 Da or less provide improved flowability, making such polymers easier to handle and load into uncoated capillaries.

In certain embodiments, the surface interaction component of the compositions of the invention comprises one or more non-crosslinked polymer. Such components may belong to a variety of chemical classes, such as those described in the following references: Molyneux, Water-Soluble Synthetic Polymers: Properties and Behavior, Volumes I and II (CRC Press, Boca Raton, 1982); Davidson, Editor, Handbook of Water-Soluble Gums and Resins (McGraw-Hill, New York, 1980); Franks, editor, Water: A Comprehensive Treatise (Plenum Press, New York, 1973); and the like.

Exemplary non-crosslinked polymers that may be suitable as a surface interaction component include polyvinylpyrrolidone, N,N-disubstituted polyacrylamide, N-monosubstituted polyacrylamides, and the like. In certain embodiments the surface interaction component comprises poly(N,N-dimethylacrylamide)(pDMA) in the range of 0.05–0.5%, preferably 0.1–0.4%, and most preferably 0.2%.

Exemplary N-substituents of the N-substituted polyacrylamides include $C_1$ to $C_{12}$ alkyl; halo-substituted $C_1$ to $C_{12}$ alkyl; methoxy-substituted $C_1$ to $C_{12}$ alkyl; hydroxyl-substituted $C_1$ to $C_{12}$ alkyl and the like. Preferably, the halo substituent is fluoro and the hydroxyl-substituted $C_1$ to $C_{12}$ alkyl is monosubstituted. It is understood that the above monomer substituents are typically selected so that the resulting polymer is water soluble. For example, the $C_{12}$ alkyl-containing monomer is often only present as a small fractional component of a copolymer. More preferably, exemplary substituents are selected from the group consisting of $C_1$ to $C_3$ alkyl; halo-substituted $C_1$ to $C_3$ alkyl; methoxy-substituted $C_1$ to $C_3$ alkyl; and hydroxyl-substituted $C_1$ to $C_3$ alkyl. Such polymers are synthesized by conventional techniques, e.g., as disclosed in Odian, Principles of Polymerization, Third Edition (John Wiley, New York, 1991), Glass, editor, Water-Soluble Polymers: Beauty and Performance (Adv. Chem. Ser., #213, American Chemical Society, Washington, D.C., 1986), and Molyneux, Water-Soluble Polymers: Properties and Behavior, Vols. I & II (CRC Press, Boca Raton, Fla., 1982).

A preferred surface interaction component is pDMA. According to certain embodiments, hydrophobic polymers other than pDMA can be used as the surface interaction component. They include, but are not limited to, the following homopolymers: N-alkyl-substituted acrylamides and their copolymers,

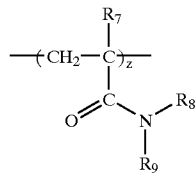

where $R_7$ can be —H or —$CH_3$, $R_8$ and $R_9$ can be independently —H, —$CH_3$, —$CH_2CH_3$, —$CH_2CH_2CH_3$, —CH($CH_3$)$_2$, or —$CH_2CONH_2$, and z ranges from about 2000 to 50,000. The average molecular weight ranges from 200,000 Da to 5,000,000 Da, preferably 300,000 Da to 2,500,000 Da. The amide group can also be cyclic compounds such as

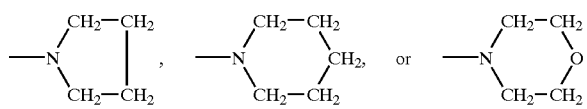

Another example of copolymers that can be used as a surface interaction component include the following structure,

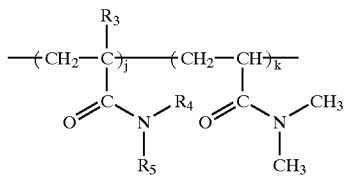

where, $R_3$, $R_4$, $R_5$, and the molecular weight have been described previously, and the ratio of j:k ranges from 1:9 to 9:1.

In certain embodiments, the polymers comprising the surface interaction component of the separation medium may be present at a concentration of from about 0.001% to about 10% weight:weight (w:w). Preferably, such polymers are present at a concentration in the range of about 0.01% to about 1% w:w.

In certain embodiments, the composition may comprise additional components such as denaturants. Such denaturants may be useful when it is desirable to prevent the formation of duplexes or secondary structures, for example, with analytes comprising polynucleotides. Exemplary, denaturants include formamide, e.g., 40–90%, urea, e.g., 6–8 M, commercially available lactams, such as pyrrolidone, 2-pyrollidinone, and the like. In certain embodiments, denaturants include urea, formamide, or 2-pyrollidinone, alone or in combination. Guidance for the use of denaturants in electrophoresis can be found in well known molecular biology references, e.g., Sambrook et al., Molecular Cloning: A Laboratory Manual, Second Edition (Cold Spring Harbor Laboratory, New York, 1989).

In certain embodiments, the composition has a viscosity of less than 10,000 centipoise (cp) at 25° C. In other embodiments the composition viscosity is less than 5,000 cp at 25° C., less than 1,000 cp at 25° C., or less than 600 cp at 25° C. All viscosity measurements were made using a Brookfield Model DV-II viscometer (Brookfield Engineering Laboratories, Inc., Middleboro, Mass.). For compositions having viscosities less than 4000 cp, spindle No. 18 was used with the small sample adapter. The spindle speed was 3 rpm for samples with a viscosity of less than 1000 cp, 1.5 rpm for samples with viscosity of between 1000 and 2000 cp, and 0.6 rpm for samples with a viscosity between 2000 and 4000 cp. For samples of viscosity over 4000 cp a smaller spindle and different adapter are necessary.

Apparatuses for carrying out capillary electrophoresis are well-known. Many references are available describing basic apparatuses and several capillary electrophoresis instruments are commercially available, e.g., the Applied Biosystems (Foster City, Calif.) model 270A, 310, 3100, or 3700 instruments. Exemplary references describing capillary electrophoresis apparatus and their operation include Jorgenson, Methods: A Companion to Methods in Enzymology, 4: 179–190 (1992); Colburn et al., Applied Biosystems Research News, issue 1 (winter 1990); Grossman et al. (cited above); and the like.

In certain embodiments, a buffer system is employed to control pH and as a charge-carrying component. Exemplary buffers include: aqueous solutions of organic acids, such as citric, acetic, or formic acid; zwitterionics, such as TES (N-tris[hydroxymethyl]-2-aminoethanesulfonic acid, BICINE (N,N-bis[2-hydroxyethyl]glycine, ACES (N-[2-Acetamido]-2-aminoethanesulfonic acid), TAPS (N-tris [Hydroxymethyl]methyl-3-aminopropanesulfonic acid) or glycylglycine; inorganic acids, such as phosphoric; and organic bases, such as Tris (Tris[hydroxymethyl] aminomethane) buffers, e.g., available from Sigma or Calbiochem. Buffer concentration can vary widely, for example between about 1 mM to 1 M. In certain embodiments, exemplary buffer solutions for use in the capillary electrophoresis methods of the invention include: (i) 100 mM TAPS, 7 M urea, pH 8.0; or (ii) TTE (50 mM Tris–50 mM TAPS), 7 M urea, pH 8.0.

In certain embodiments, double-stranded polynucleotides, e.g., DNA fragments from PCR or LCR amplifications, enzyme digests, or the like, are separated by standard protocols, or manufacturer's suggested protocols where a commercial capillary electrophoresis instrument is employed, e.g., a model 270-HT, 310, 3100, or 3700 instrument (Applied Biosystems, Foster City). An exception to such standard or suggested protocols is that the compositions and/or capillary electrophoresis elements of the invention are employed. In certain embodiments, a method for separating analytes by capillary electrophoresis comprises inserting into an uncoated capillary, having a first and a second end, a composition comprising a sieving component and a surface interaction component. A sample of different sized analytes is loaded in the capillary and an electric field is applied between the first and second ends of the capillary. The different sized analytes in the sample migrate through the composition within the capillary, separating the analytes. In other embodiments, a precoated capillary is used. In certain embodiments, the composition comprises one of the compositions disclosed herein.

Certain of the methods of the invention can be employed for DNA sequencing. In certain embodiments, such sequencing involves separation of single stranded polynucleotides prepared by DNA sequencing protocols. Detailed descriptions of DNA sequencing protocols can be found, among other places, in Automated DNA Sequencing Chemistry Guide (Applied Biosystems, Part No. 4305080); Sambrook et al., Molecular Cloning: A Laboratory Manual, Second Edition (Cold Spring Harbor Laboratory, New York, 1989); Ausbel et al., Current Protocols in Molecular Biology (John Wiley & Sons, 1993, including supplements through August 2000); or the like.

An important feature of certain currently available DNA sequencing protocols is the generation of a "nested series" or "ladder" of single-stranded polynucleotides or DNA sequencing fragments, that may be separated by size. The chain-termination methods of DNA sequencing may comprise (1) providing an oligonucleotide primer and a template nucleic acid containing, a target nucleic acid whose sequence is to be determined, (2) hybridizing the oligonucleotide primer to the template nucleic acid, (3) extending the primer with a nucleic acid polymerase, e.g., T7 DNA polymerase, Sequenase™, reverse transcriptase, or the like, in a reaction mixture containing nucleoside triphosphate precursors and at least one chain terminating nucleotide to form a nested series of DNA fragment populations, such that every shorter DNA fragment is a subsequence of every longer DNA fragment and such that each DNA fragment of the same size terminates with the same chain-terminating nucleotide, (4) separating the DNA fragment populations according to size, and (5) identifying the chain-terminating nucleotide associated with each DNA fragment population. The skilled artisan will appreciate, however, that many variations on DNA sequencing methods are available.

Acceptable templates include those discussed in the art, e.g., Technical Manual for ABI Model 370A DNA Sequencer (Applied Biosystems, Foster City, Calif.). For example, the target sequence may be inserted into a suitable cloning vector, such as the replicative form of an M13 cloning vector, which is then propagated to amplify the number of copies of the target sequence. The single-stranded form of M13 is isolated for use as a template. Also, a template can be provided by polymerase chain reaction (PCR) as taught in the art, e.g., Innis et al., (cited above); Wilson et al., Biotechniques, Vol. 8, pgs. 184–189 (1990); Gyllensten, Biotechniques, Vol.7, pgs. 700–708 (1989); and the like. After amplification, in certain embodiments, the template can be used in the polymerization reaction(s) either in liquid phase or attached to a solid phase support, e.g., as taught by Stahl et al, Nucleic Acids Research, Vol. 16, pgs. 3025–3038 (1988); Hultman et al., Nucleic Acids Research, Vol. 17, pgs. 4937–4946 (1989); or the like.

Once the nested series DNA fragments are generated, they are separated by capillary electrophoresis using the compositions, capillary electrophoresis elements, or methods of the invention.

The invention, having been described above, may be better understood by reference to examples. The following examples are intended for illustration purposes only, and should not be construed as limiting the scope of the invention in any way.

EXAMPLES

Example 1

Preparation of a Non-crosslinked Acrylamide Polymer by Solution Polymerization

A solution containing 94.50 g distilled water (18 M ohm-cm) and 32.02 g (0.129 mol) of a 28.57 wt % acrylamide solution (Bio-Rad, Hercules, Calif.) was prepared in a 500-mL three-necked round bottom flask fitted with a 2" Teflon blade for mechanical stirring, a bleeding tube for purging, and a thermometer. Ultrapure helium (99.99%) was bubbled into the solution, with constant mechanical stirring, at a rate of 150 mL/min for 120 minutes, to deoxygenate the solution. To this deoxygenated solution, 1.0 mL (13.06 mmol) of 2-propanol (isopropanol) and 4.0 mL (0.35 mmol) of a 1.99 wt % ammonium persulfate (99.99% pure, Aldrich) solution were added with syringes. The flask was immersed in an oil bath at 50±1° C. for 120 minutes with constant mechanical stirring at 150 rpm and helium purging at 150 ml/minute. The reaction was quenched by the addition of 200 mL of distilled water with stirring and bubbled with air for 10 minutes. The resulting water-clear solution was placed in a regenerated 50 K molecular weight cutoff (MWCO) Spectra/Por-7 cellulose membrane and dialyzed against 4.5 gallons of distilled (18 M ohm-cm) water for three days. The water was changed twice daily. The dialyzed solution was lyophilized and 8.41 g of non-crosslinked acrylamide polymer was obtained (92% yield).

This polymer was characterized by gel permeation chromatography (GPC) using polyacrylamide primary standards by American Polymer Standards (Mentor, Ohio). Separations were performed at 30° C. with three chromatography columns in series, an Ultrahydrogel (Waters Corp., Milford, Mass.) 2000 Angstrom column, an Ultrahydrogel 1000 Angstrom column, and a guard column, using 0.05M $NaNO_3$, at a flow rate of 1 ml/min. The injection volume was 100 $\mu$l and the detector was a Knauer DRI 8X. This non-crosslinked acrylamide polymer was found to have a $M_n$ of 589 kilodaltons (kDa), a $M_w$ of 2517 kDa (2.5 M in FIGS. 1–3), and a polydispersity of 4.23. The $M_w$, as determined by batch mode light scattering, was 1936 kDa (Prep. No. 1 in Table 1). The skilled artisan will appreciate that the observed molecular weight of a polymer may vary depending on the method of characterization. The molecular weights recited in the appended claims are based on the GPC method described above.

The polymer was vacuum dried at 40° C. for at least 4 hours prior to use.

Example 2

Preparation of Another Non-crosslinked Acrylamide Polymer by Solution Polymerization A second non-crosslinked acrylamide polymer was prepared as described in Example 1, except that 2.0 mL (26.12 mmol) of isopropanol were added to the deoxygenated solution. The skilled artisan will understand that isopropanol serves as a chain transfer agent, limiting the molecular weight of the polymer as it is prepared. Thus, by varying the amount of isopropanol, the molecular weight of the polymer may be altered.

The resulting water-clear solution was dialyzed and lyophilized, as in Example 1. The yield was 9.0 g of non-crosslinked acrylamide polymer (98% yield). The polymer was characterized by gel permeation chromatography and was found to have a $M_n$ of 310 kDa, a $M_w$ of 1376 kDa (1.4 M in FIGS. 1–3), and a polydispersity of 4.40. The $M_w$ as determined by batch mode light scattering was 975 kDa. (Prep. No. 2 in Table 1).

Following the in the solution polymerization procedure described in Example 1 and 2, additional non-crosslinked acrylamide polymers with different molecule weights were prepared by varying the concentration of iso-propanol (see Table 1, Prep. Nos. 1–4).

TABLE 1

Non-crosslinked Acrylamide Polymer Preparations.

| Prep. No. | Molar ratio [iso-propanol]:[acrylamide] | Yield (%) | Mw (Batch mode light scattering) | Mw (GPC method) |
|---|---|---|---|---|
| 1 | 0.101 | 92.0 | 1936 kDa | 2517 kDa (2.5 M) |
| 2 | 0.203 | 98.0 | 975 kDa | 1376 kDa (1.4 M) |
| 3 | 0.112 | 98.0 | 1325 kDa | 2015 kDa (2.0 M) |
| 4 | 0.406 | 82.0 | 697 kDa | 744 kDa (0.75 M) |
| 5 | N/A | — | 12500 kDa | 6377 kDa (6.4 M) |

Example 3

Preparation of a Non-crosslinked Acrylamide Polymer by Inverse Emulsion Polymerization A fifth non-crosslinked acrylamide polymer was prepared by inverse emulsion polymerization (IEP) as follows. To a 1-L polypropylene beaker was added 100.05 g of Petrolum Special (bp 180–220 ° C., Fluka), 100.01 g of a 28.57 wt % acrylamide solution (Bio-Rad), 2.50 g of sorbitan monooleate (Fluka), and 1.00 mL of a 1.0109 wt % solution of ammonium persulfate (99.99%, Aldrich). The mixture was emulsified by stirring with a 2" magnetic stir bar for 10 minutes at 800 rpm. The emulsion was then transferred into a 1-L three-necked round bottom flask equipped with a 2" Teflon stirring blade for mechanical stirring, a bleeding tube for purging, and a thermometer. The emulsion was purged with ultra pure helium (99.99%) at a rate of 150 mL/min for 120 minutes with constant mechanical stirring at 300 rpm. To the emulsion was added 0.010 mL of N,N,N,N-tetramethylethylenediamine (ultra pure, Armesco) using a microsyringe. The flask was lowered into an oil bath at 35±1° C. with constant mechanical stirring at 300 rpm and helium purging at 150 mL/min for 19 hours. During polymerization, the temperature of the emulsion never exceeded 35° C.

After 19 hours, 400 mL of acetone was added and the emulsion was stirred at 300 rpm for 2 hours. The polymer powder was allowed to precipitate and the supernatant layer was decanted. To the precipitated polymer, 300 mL of acetone was added, the mechanical stirrer was replaced by a 1.5" egg-shaped magnetic stir bar, and stirred at 800 rpm for 3 hours. The precipitated polymer became a very fine powder. This powder was allowed to settle and the organic layer decanted. The polymer powder was triturated with 300 mL of acetone and stirred at 800 rpm for another 3 hours. The polymer was suction filtered and rinsed with a copious amount of acetone. Approximately 5.4 grams of wet polymer powder was added to 450 mL of distilled water and the solution was stirred with a 1" magnetic stir bar at 75 rpm for two days. The resulting mixture was divided into five 50-mL Falcon tubes and tumbled for two days to yield a very viscous solution. This solution was placed in a regenerated 50K MWCO Spectra/Por-7 cellulose membrane and dialyzed against 4.5 gallons of distilled water (18 M ohm-cm) for three days. The water was changed twice daily. The dialyzed solution was lyophilized to give 4.50 g of non-crosslinked acrylamide polymer. The $M_w$, as determined by batch mode light scattering, was 12500 kDa, and as determined by gel permeation chromatography, was 6377 kDa (Prep. 5 in Table 1; 6.4 M in FIGS. 1–3).

Example 4

Preparation of Exemplary Sieving Components

Exemplary sieving components for use in the compositions of the invention were prepared as follows. One hundred milligrams of any of the non-crosslinked acrylamide polymers shown in Table 1 was added to 2.44 grams of water, 0.075 grams of 12.3% pDMA solution, and 0.5 grams of 1 M Na-TAPS/10mM EDTA buffer, pH 8.0. The mixture was dissolved by rotating on a rotor wheel overnight. Following this procedure, five different sieving components, each comprising a different non-crosslinked acrylamide polymer shown in Table 1, were prepared.

Example 5

Separation of Analytes by Capillary Electrophoresis

Five exemplary compositions for separating analytes were prepared by combining one of the five sieving components from Example 4 with 0.2% pDMA. These five compositions were analyzed to evaluate their ability to separate polynucleotide analytes using an ABI 310 capillary electrophoresis apparatus (Applied Biosystems, Foster City, Calif.) with 47 cm uncoated capillaries (36 cm from the injection end to the detector). Capillary electrophoresis elements were prepared by pumping one of the five compositions through uncoated capillaries for 400 seconds before each analysis.

Analytes, comprising fluorescently labeled DNA sequencing fragments and a single-stranded DNA sequencing ladder, including 18 DNA fragments of known size, labeled with the fluorescent dye TET, were dissolved in formamide. This analyte solution was injected into the capillary electrophoresis elements at 1.5 kV for 10 seconds. Separations were performed at run temperatures of 50° C., 60° C., or 70° C., using an electric field of 200 V/cm.

Figure 2:
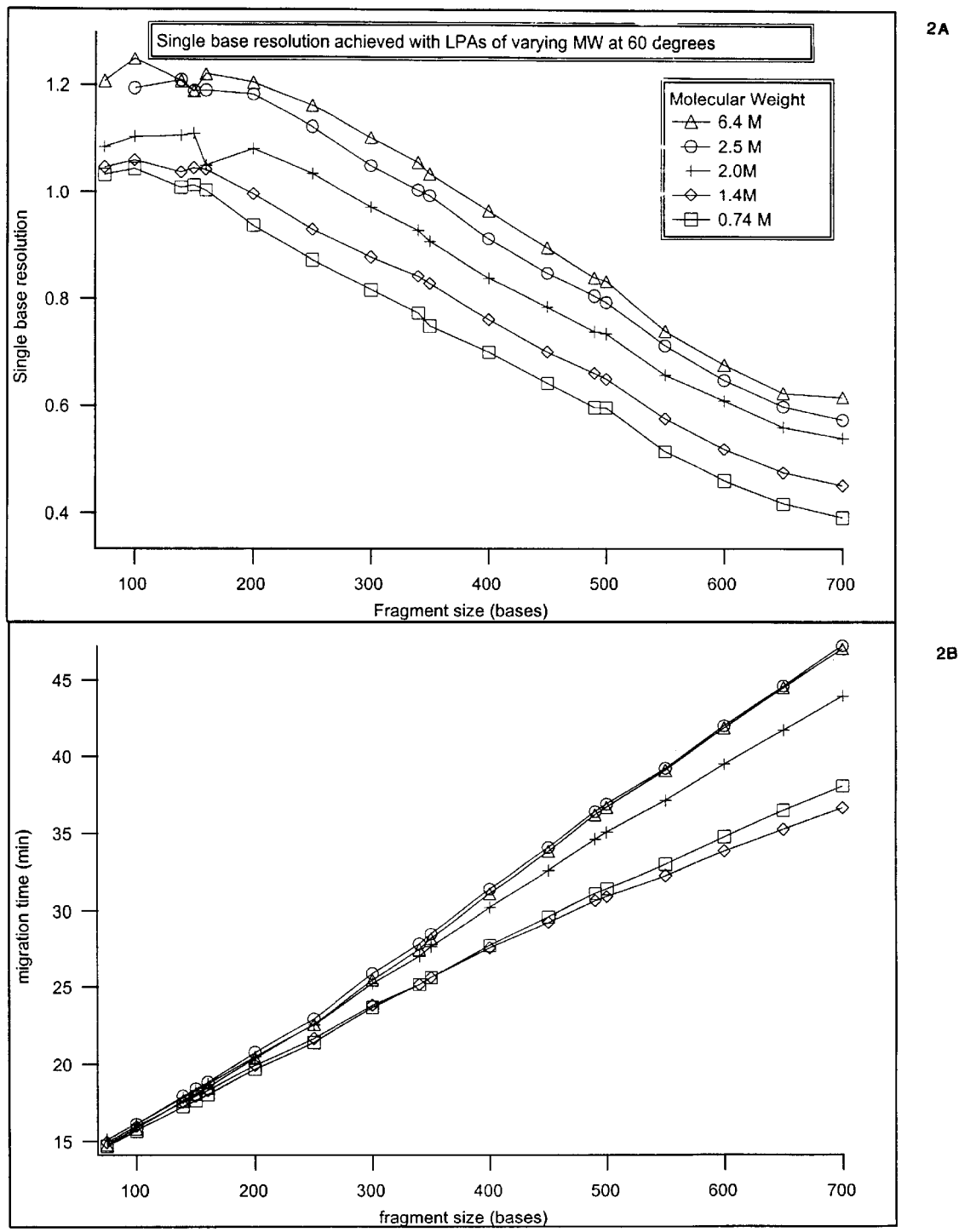
FIG. 2 illustrates single base resolution data collected by capillary electrophoresis of labeled polynucleotide ladders using the same five compositions described in FIG. 1, but at a run temperature of 60° C.
Figure 3:
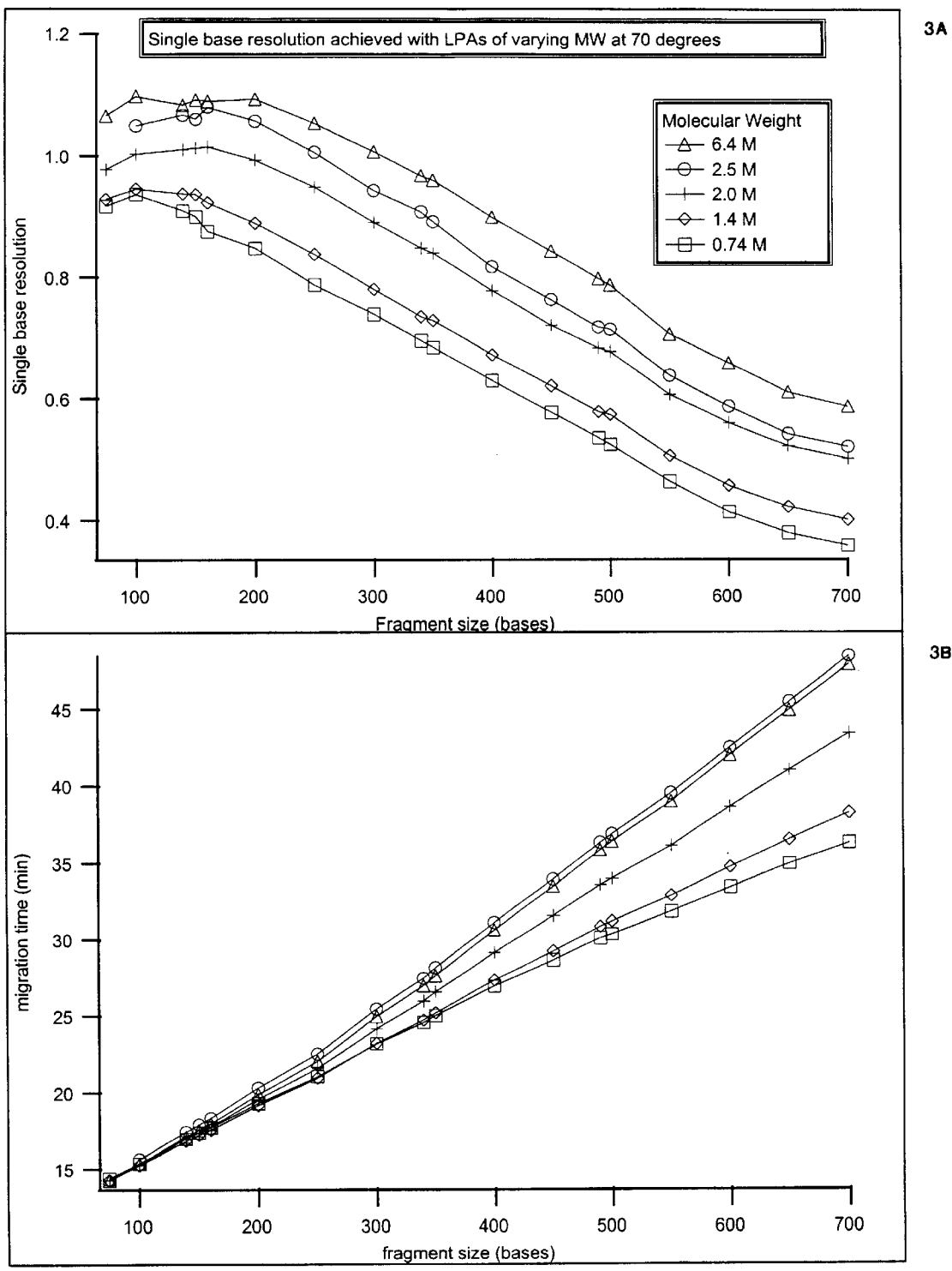
FIG. 3 illustrates single base resolution data collected by capillary electrophoresis of labeled polynucleotide ladders using the same five compositions described in FIG. 1, but at a run temperature of 70° C.

The peak width (defined as 4 times the standard deviation of a Gaussian peak) and migration time of peaks from the DNA sequencing ladder and fragments were measured. These values were used to calculate single base resolution values. The single base resolution value and migration time for three or four replicate runs performed at each of the run temperatures is shown in FIGS. 1, 2, and 3.

Figure 4:
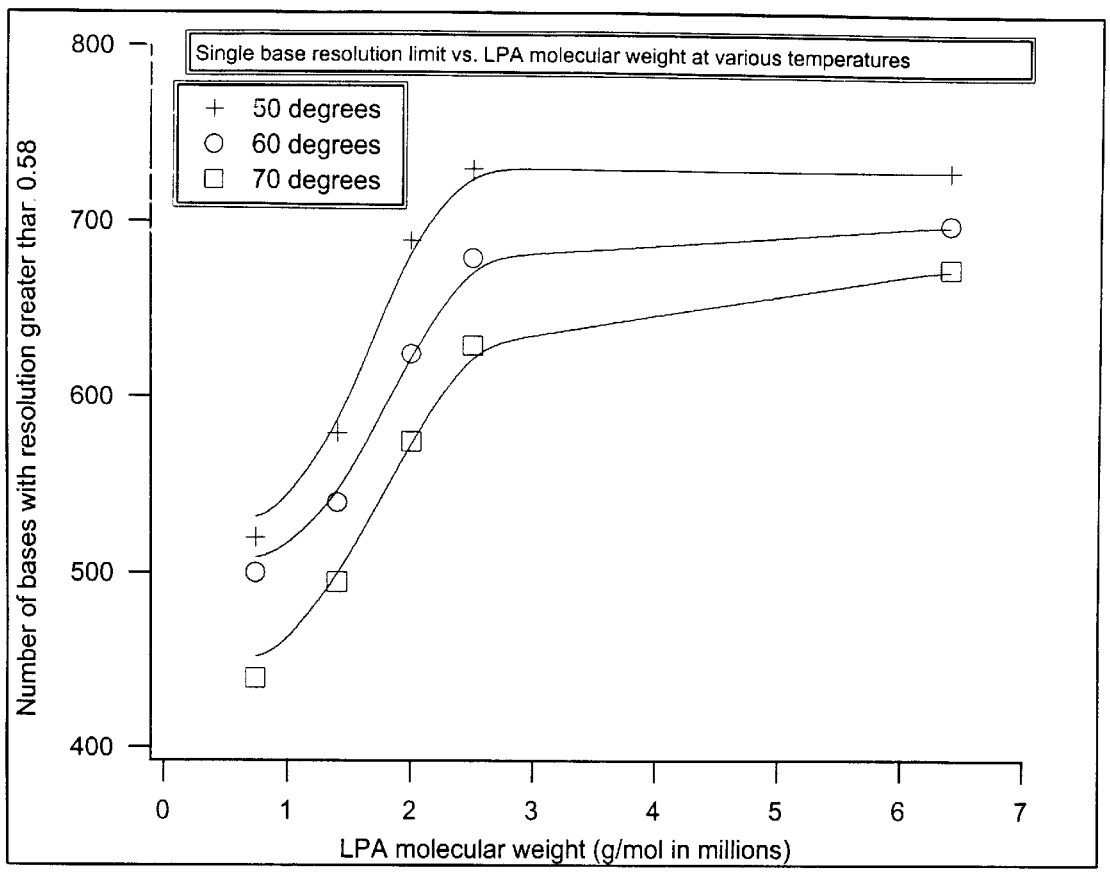
FIG. 4 illustrates the single base resolution limit observed using compositions comprising the five sieving components described in FIG. 1 at run temperatures of 50° C., 60° C., or 70° C. The single base resolution limits were estimated by visual inspection of the single base resolution data depicted in FIGS. 1, 2, and 3.

The single base resolution limit for the five compositions and the three run temperatures are shown in FIG. 4. Regardless of run temperature, the single base resolution increases as the polymer molecular weight increase until about 3,000,000 Da (see FIG. 4). Each of the three run temperature curves plateau, however, when the polymer molecular weight increases above about 3,000,000 Da. Thus, increasing the molecular weight of the polymer above about 3,000,000 Da does not noticeably increase the single base resolution. Increasing the molecular weight of the polymer above about 3,000,000 Da does, however, cause a rapid increase in viscosity of the polymer solution. For example, the viscosity of the 2,500,000 Da polymer used in the Examples was approximately 500 centipoise, while the viscosity of the 6,400,000 Da polymer was greater than 50,000 centipoise. Thus, sieving compositions with molecular weights of 1,000,000 to 3,000,000 Da provide efficient single base resolution while retaining sufficiently low viscosity for capillary loading.

Although the invention has been described with reference to various applications, methods, and compositions, it will be appreciated that various changes and modifications may be made without departing from the invention. The foregoing examples are provided to better illustrate the invention and are not intended to limit the scope of the invention.

What is claimed is:

1. A method for separating analytes by capillary electrophoresis comprising:

separating the analytes by capillary electrophoresis in a composition comprising: a sieving component comprising a non-crosslinked acrylamide polymer having a molecular weight greater than 1,000,000 Da and less than or equal to about 3,000,000 Da; and a surface interaction component comprising one or more non-crosslinked polymers selected from the group consisting of poly(meth)acrylamide, N,N-disubstituted polyacrylamide and N-substituted polyacrylamide, wherein said N-substituents are selected from the group consisting of $C_1$ to $C_3$ alkyl, halo-substituted $C_1$ to $C_3$ alkyl, methoxy-substituted $C_1$ to $C_3$ alkyl, and hydroxyl-substituted $C_1$ to $C_3$ alkyl; wherein the sieving component and the surface interaction component are the same or different; and wherein the composition does not include a crosslinked polymer gel wherein the non-crosslinked acrylamide polymer has a viscosity of less than 1,000 centipose at 25° C.

2. The method of claim 1, which is carried out in parallel with a plurality of uncoated capillaries.

3. The method of claim 1, wherein the non-crosslinked acrylamide polymer has a viscosity of less than 500 centipoise at 25° C.

4. The method of claim 1, wherein the composition further comprises at least one denaturant.

5. The method of claim 4, wherein the at least one denaturant is selected from the group consisting of at least one of formamide, urea and 2-pyrollidinone.

6. The method of claim 5, wherein the at least one denaturant comprises urea.

7. A method for separating analytes by capillary electrophoresis comprising: separating the analytes by capillary electrophoresis with a capillary electrophoresis element comprising:

an uncoated capillary;

a composition for separating analytes located within the uncoated capillary, the composition comprising: a sieving component comprising a non-crosslinked acrylamide polymer having a molecular weight greater than 1,000,000 Da and less than or equal to about 3,000,000 Da and having a viscosity of less than 1,400 centipoise at 25° C.; and a surface interaction component;

wherein the surface interaction component comprises a solution of one or more non-crosslinked polymers; and wherein the capillary electrophoresis element does not include a crosslinked polymer gel.

8. The method of claim 7, which is carried out in parallel with a plurality of uncoated capillaries.

9. The method of claim 8, wherein the uncoated capillaries comprise silica, fused silica, quartz, silicate-based glass, phosphate glass, or alumina-containing glass.

10. The method of claim 8, wherein the uncoated capillaries are plastic channel capillaries.

11. A method for separating analytes by capillary electrophoresis comprising: separating the analytes by capillary electrophoresis with a capillary electrophoresis element comprising:

an uncoated capillary;

a composition for separating analytes located within the uncoated capillary, the composition comprising: a sieving component comprising a non-crosslinked acrylamide polymer having a molecular weight greater than 1,000,000 Da and less than or equal to about 3,000,000 Da and having a viscosity of less than 600 centipoise at 25° C.; and a surface interaction component comprising poly(N,N-dimethylacrylamide): and a denaturant comprising urea;

wherein the surface interaction component comprises a solution of one or more non-crosslinked polymers; and wherein the capillary electrophoresis element does not include a crosslinked polymer gel.

12. The method of claim 11, which is carried out in parallel with a plurality of capillaries.

13. The method of claim 12, wherein the capillaries comprise silica, fused silica, quartz, silicate-based glass, phosphate glass, or alumina-containing glass.

14. The method of claim 12, wherein the capillaries are plastic channel capillaries.

15. A method for separating analytes by capillary electrophoresis comprising:

inserting into an uncoated capillary having a first end and a second end a composition comprising a sieving component comprising an uncrosslinked acrylamide polymer having a molecular weight greater than 1,000,000 Da and less than or equal to about 3,000,000 Da and a viscosity of less than 1,000 centipose at 25° C. and a surface interaction component comprising one or more non-crosslinked polymers selected from the group consisting of poly(meth)acrylamide, N,N-disubstituted polyacrylamide and N-substituted polyacrylamide, wherein said N-substituents are selected from the group consisting of $C_1$ to $C_3$ alkyl, halo-substituted $C_1$ to $C_3$ alkyl, methoxy-substituted $C_1$ to $C_3$ alkyl, and hydroxyl-substituted $C_1$ to $C_3$ alkyl; wherein the sieving component and the surface interaction component are the same or different; wherein the composition does not include a crosslinked polymer gel;

loading a sample of different sized analytes in the capillary; and applying an electrical field between the first and second ends of the capillary so that the different sized analytes in the sample migrate through the capillary, thereby separating the analytes.

16. The method according to claim 15, wherein the composition further comprises at least one denaturant.

17. The method of claim 16, wherein the at least one denaturant comprises urea.

18. The method according to claim 15, wherein the surface interaction non-crosslinked polymer is poly(N,N-dimethylacrylamide).

19. The method of claim 15, which is carried out in parallel with a plurality of uncoated capillaries.

20. The method of claim 19, wherein the uncoated capillaries comprise silica, fused silica quartz, silicate-based glass, phosphate glass, or alumina-containing glass.

21. The method of claim 19, wherein the uncoated capillaries are plastic channel capillaries.

* * * * *